United States Patent [19]

Magee

[11] 4,154,733

[45] May 15, 1979

[54] KETOXIME CARBAMATES

[75] Inventor: Thomas A. Magee, Mentor, Ohio

[73] Assignee: Diamond Shamrock Corporation, Cleveland, Ohio

[21] Appl. No.: 909,276

[22] Filed: May 24, 1978

Related U.S. Application Data

[60] Division of Ser. No. 801,585, May 31, 1977, Pat. No. 4,118,389, which is a continuation-in-part of Ser. No. 553,648, Feb. 27, 1975, Pat. No. 4,028,413, which is a continuation-in-part of Ser. No. 229,207, Feb. 24, 1972, Pat. No. 3,875,232, which is a continuation-in-part of Ser. No. 132,584, Apr. 8, 1971, abandoned.

[51] Int. Cl.$^2$ .................... A01N 9/12; C07D 277/08; C07D 277/20

[52] U.S. Cl. .................... 260/302 S; 424/270; 424/DIG. 8

[58] Field of Search .................. 424/270, DIG. 8; 260/302 S

[56] References Cited

U.S. PATENT DOCUMENTS

| | | | |
|---|---|---|---|
| 3,217,037 | 11/1965 | Payne, Jr. et al. | 260/566 |
| 3,507,965 | 4/1970 | Payne, Jr. et al. | 424/327 |

*Primary Examiner*—Allen J. Robinson
*Attorney, Agent, or Firm*—John C. Tiernan

[57] ABSTRACT

Carbamate derivatives of ketoximes are useful in combatting pests such as insects, mites, and nematodes.

4 Claims, No Drawings

KETOXIME CARBAMATES

CROSS REFERENCE TO RELATED APPLICATION

This application is a division of copending application Ser. No. 801,585 filed May 31, 1977 which will issue Oct. 3, 1978 as U.S. Pat. No. 4,118,389 which was continuation-in-part of copending application Ser. No. 553,648, filed Feb. 27, 1975, now U.S. Pat. No. 4,028,413 said application Ser. No. 553,648 being a continuation-in-part of application Ser. No. 229,207, filed Feb. 24, 1972, now U.S. Pat. No. 3,875,232, and said application Ser. No. 229,207 being a continuation-in-part of application Ser. No. 132,584, filed Apr. 8, 1971, now abandoned, the specifications and claims of which are specifically incorporated herein by reference.

BACKGROUND OF THE INVENTION

1. Field of the Invention

This invention relates to organic compounds useful as pesticides and more particularly to carbamate derivatives of ketoximes having insecticidal, miticidal, and, in some cases, nematocidal activity comparable or superior to the most closely related commercial products while having significantly lower toxicity toward mammals than these commercial products.

2. Description of the Prior Art

The outstanding pesticidal activity of the carbamate derivatives of the ketoximes disclosed in this invention is surprising and unexpected because the prior art indicates that carbamate derivatives only of substituted aldoximes have high pesticidal activity, whereas ketoxime derivatives were essentially inactive. For example, U.S. Pat. No. 3,217,037 and U.S. Pat. No. 3,507,965 show compounds, possessing pesticidal activity, of the structure:

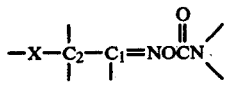

wherein $X=O$ or $S(O)_n$ when $n=0$, 1, or 2 and the free valences are satisfied by hydrogen or hydrocarbyl radicals. In these two patents, the preferred compounds are aldoximes wherein the carbon atom ($C_1$) attached to the oxime moiety in the above structure is substituted with hydrogen. In the J. Agr. Food Chem,. 14, 356 (1966), the patentees of these patents state, "The data . . . demonstrate . . . the detrimental effect . . . of replacing the aldehydic hydrogen with an alkyl group. All of the ketoxime derivatives . . . were virtually inactive when compared with the aldoxime derivative . . ." Ketoxime compounds of Formulas (I) and (II) below are reported in the reference as being essentially inactive compared to the aldoxime compound of Formula (III) below which is known commercially as aldicarb (Temik). The compound of Formula (II) differs from the compound of Formula (III) only in that a methyl group has been substituted for the aldehydic hydrogen of Formula (III).

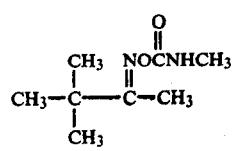

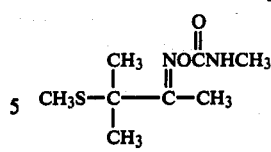

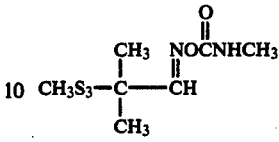

The ketoxime compounds of Formulas (I) and (II) have been resynthesized and tested and their reported lack of activity relative to that of the compound of Formula (III) reconfirmed. Surprisingly, however, the ketoxime derivatives of the present invention have been found to possess high pesticidal activity, comparable or superior to that of the compound of Formula (III).

SUMMARY OF THE INVENTION

The carbamates of ketoximes of the present invention can be represented by the formula:

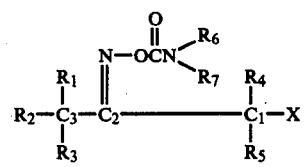

Where:
- $R_1 = R_2-R_3$ or X;
- $R_2-R_3$ = hydrogen, lower alkyl, lower alkenyl, alkynyl, substituted lower alkyl, alkenyl, or alkynyl with the proviso that $R_2$ and $R_3$ may be connected to form a cycloaliphatic ring;
- $R_4-R_5$ = hydrogen;
- $R_6-R_7$ = hydrogen, lower alkyl, lower alkenyl, lower alkynyl;
- $X = SR_8$, $S(O)R_8$, $SO_2R_8$, $OR_8$, $OSO_2R_8$, $NR_8R_9$, $NO_2$, CN, SCN, $N_3$, or halogen;
- $R_8$ = hydrogen, lower alkyl, lower alkenyl, lower alkynyl, aryl, substituted aryl, carbamyl, substituted carbmyl, acyl, or substituted acyl with the proviso that the lower alkyl or alkenyl groups may be further substituted with X; and
- $R_9$ = hydrogen or lower alkyl with the proviso that $R_8$, $R_9$ and N in the $NR_8R_9$ group may form a heterocyclic ring.

The term lower alkyl radical means a radical having from one to about seven carbon atoms.

This invention specifically includes those carbamates of Formula (IV) where $R_2$ and $R_3$ are lower alkyl radicals such as methyl; $R_1$ is hydrogen, or X: $R_6$ and $R_7$ are individually hydrogen, a lower alkyl radical such as methyl or a lower alkenyl radical; X is $—S(O)_nR_8—Y$ where $n=0$, 1, or 2; $R_8$ is a lower alkylene radical; and Y is selected from the group consisting of $SR_9$, $S(O)R_9$, $SO_2R_9$, $OSO_2R_9$, SCN, haloalkyl, alkoxy, acyl, alkoxy carbonyl, carboxylate, and carboxyl, with the proviso that Y, either alone, or in combination with $R_8$, can be in the form of a cyclic radical, selected from the group consisting of thiophene, thiazine, pyridene, and $R_9$ is selected from the group consisting of hydrogen, lower alkyl, lower alkenyl, lower alkynyl, aryl, carbamyl, acyl, or haloalykl.

It is completely unexpected to discover that carbamate derivatives of ketoximes such as carbamate of Formula (V) have pesticidal activity comparable to that of the carbamate derivative of the aldoxime of Formula (III):

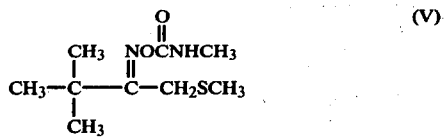

and simultaneously exhibit significantly lower toxicity toward mammals than does the compound of Formula (III). Thus, the oral toxicity of the compound of Formula (V), measured on albino rats and expressed as the $LD_{50}$, was found to be 8.5 mgm/kg of body weight; the dermal toxicity, measured on albino rabbits, again expressed as the $LD_{50}$, was 38.9 mgm/kg of body weight. $LD_{50}$ is a standard means of expressing toxicity and indicates the concentration required to kill 50% of the test animals. In each case, the $LD_{50}$ value is approximately eight times greater than the reported value for the carbamate derivative of the aldoxime compound of Formula (III).

It is an object of this invention to provide carbamates of substituted ketoximes, which are useful pesticides. A further object is to provide a method for producing these carbamates. Still another object is to provide methods for controlling pests such as insects, mites, and nematodes using these carbamates. It is intended, however, that the detailed description and specific examples given herein do not limit this invention but merely indicate preferred embodiments thereof since various changes and modifications within the scope of this invention will become apparent to those skilled in the art.

DESCRIPTION OF THE PREFERRED EMBODIMENTS

Preferred compounds of Formula (IV) include those carbamates of Formula (IV) where $R_2$ and $R_3$ are lower alkyl radicals such as methyl; $R_1$ is $R_2$ or hydrogen; $R_6$ and $R_7$ are individually hydrogen, a lower alkyl radical such as methyl or a lower alkenyl radical; X is $-S(O)_n-R_8-Y$ where n=0, 1, or 2; $R_8$ is a lower alkylene radical; where Y, either alone, or in combination with $R_8$, is a cyclic radical, selected from the group consisting of thiazole, pyridine, pyrimidine, imidazol and thiadiazol, including compounds when such cyclic radicals are halogen and/or lower alkyl substituted.

These compounds exhibit extremely high activity as insecticides and miticides, both as contact and as systemic toxicants. In some cases, they show high nematocidal activity.

As specific examples of these compounds, there may be mentioned:

3,3-Dimethyl-1-(2-pyridylthio)-2-butanone O-Methylcarbamyloxime
3,3-Dimethyl-1-(4-pyridylthio)-2-butanone O-Methylcarbamyloxime
3,3-Dimethyl-1-(4-tertbutylthiazol-2-yl)thio-2-butanone O-Methylcarbamyloxime
3,3-Dimethyl-1-(2-pyrimidinylthio)-2-butanone O-Methylcarbamyloxime
3,3-Dimethyl-1-(4-methylpyrimidin-2-yl)thio-2-butanone O-Methylcarbamyloxime
3,3-Dimethyl-1-(4,5-dihydrothiazol-2-yl)thio-2-butanone O-Methylcarbamyloxime
3,3-Dimethyl-1-(2-pyridylsulfonyl)-2-butanone O-Methylcarbamyloxime
3,3-Dimethyl-1-(4-methylthiazol-2-yl)thio-2-butanone O-Methylcarbamyloxime
3,3-Dimethyl-1-(1-oxo-2-pyridyl)thio-2-butanone O-Methylcarbamyloxime
3,3-Dimethyl-1-(1-methylimidazol-2-yl)thio-2-butanone O-Methylcarbamyloxime
3,3-Dimethyl-1-(5-meghyl-1,3,4-thiadiazol-2-yl)-thio-2-butanone O-Methylcarbamyloxime It will be appreciated by those skilled in the art that the ketoxime derivatives of this invention may exist in two geometric forms, the syn and the anti, representing the cis and trans isomers around the oxime double bond. Both isomers and their mixtures are intended to be included in the scope of this invention.

These compounds can be prepared by one of several methods. The one method (herein referred to as Method A) involves reaction of an isocyanate with an oxime as shown, for example, in the equation:

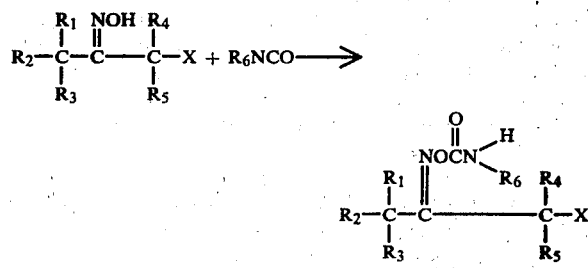

wherein $R_1$ through $R_6$ and X are defined above. The oxime and isocyanate are reacted in an inert organic solvent from about 0° C. to about 150° C., preferably from about 20° C. to about 80° C., and at a pressure from about 1 to 10 atmospheres, preferably from about 1 to about 3 atmospheres. Reaction pressure is determined by reaction temperature, concentration and vapor pressure of the isocyanate.

Any inert organic solvent used in the reaction should not contain hydroxy, amino or other groups which will react with the isocyanate function. Useful inert solvents include aliphatic and aromatic hydrocarbons, such as hexane, heptane, octane, benzene, toluene, xylene; ethers such as diethyl ether, dipropyl ether, ethylpropyl ether; esters such as ethyl acetate, ethyl propionate; ketones such as acetone, methyl ethyl ketone; and chlorinated hydrocarbons such as methylene chloride, perchloroethylene, and the like.

Preferably, reaction is carried out in the presence of from about 0.1 to about 1.0% by weight, based on the weight of reactants, of a tertiary amine catalyst such as triethyl amine, N,N-dimethylaniline, or the like.

The molar ratio of isocyanate to oxime can vary from about 0.1:1 to about 10:1. An equimolar amount or slight excess of isocyanate is preferred to ensure complete reaction of the oxime. Reaction times can vary from a few minutes to several days. Usually reaction times of from about one-half to about six hours are sufficient.

A second method (hereinafter referred to as Method B) for preparing these compounds involves reaction of an oxime with phosgene to obtain an oxime chloroformate which is then reacted with an amine. This method is illustrated in Equations (1) and (2) below:

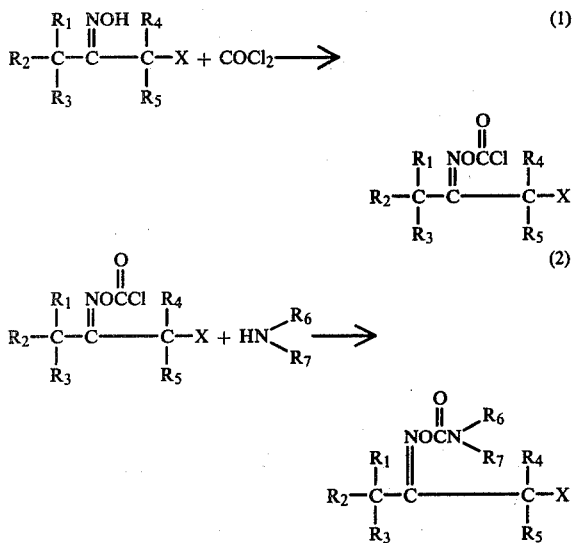

In the reaction shown in Equation (1), a solution of the oxime dissolved in an inert solvent such as diethyl ether, is added slowly to a solution of phosgene dissolved in an inert solvent in the presence of an HCl acceptor such as a tertiary amine, e.g., N,N-dimethylaniline. Reaction is carried out from about $-30°$ C. to about $100°$ C., preferably at from about $0°$ C. to about $50°$ C. The resulting reaction mixture, a solution of the chloroformate in an inert organic solvent, can be filtered or washed with water to remove amine hydrochloride before it is used in the reaction shown in Equation (2).

In the reaction shown in Equation (2), an amine is added to the chloroformate solution in the presence of an amine solvent such as water, at temperatures between about $-40°$ C. and about $80°$ C., preferably at about $0°$ C. to about $40°$ C. A larger than molar excess of amine can be used so that the amine acts both as reactant and as HCl acceptor and complete conversion of chloroformate is obtained. Alternatively, a separate HCl acceptor, such as tertiary amine, can be used.

A third method (hereinafter referred to as Method C) for the preparation of the compositions of the present invention comprises reacting:

(a) a compound of the formula

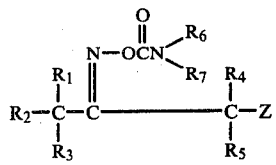

wherein Z is a reactive halogen, and (b) HX, in the presence of a HZ acceptor. This includes reaction of the haloketones with mercaptans or alcohols in the presence of an acid acceptor, e.g., sodium alkoxide. Sulfinyl and sulfonyl linked compounds can be prepared by oxidizing the appropriate sulfide linked compound with sodium metaperiodate or acidic hydrogen peroxide, respectively.

Liquid or solid carbamates produced by the above methods can be recovered from reaction mixtures by conventional means. For example, they can be recovered by removal of solvent and excess amine or isocyanate by vacuum distillation. Although these products are obtained in very pure form, they can be further purified, if desired, by recrystallization, distillation, absorption chromatography, or other known procedures.

Although the compounds of this invention can be applied in undiluted form to the plant or other material being treated, it is usually desirable to apply these compounds in admixture with either solid or liquid inert, pesticidal adjuvants. For example, the compounds can be applied to plants for pesticidal purposes by spraying the plants with aqueous or organic solvent dispersions of the compounds. Choice of an appropriate solvent is determined by factors such as concentration of active ingredient, the volatility required in the solvent, cost of the solvent, and nature of the material being treated.

Solvents, which can be employed as carriers for these compounds, which hydrocarbons such as benzene, toluene, xylene, kerosene, diesel oil, fuel oil, and naphthas; ketones such as acetone, methyl ethyl ketone and cyclohexane; chlorinated hydrocarbons such as trichloroethylene, perchloroethylene; esters such as ethyl acetate, amyl acetate and butyl acetate; ethers of glycol such as the monomethyl and monoalkyl ethers of diethylene glycol, the monoethyl ether of propylene glycol; alcohols such as ethanol, isopropanol, pentanols, and the like.

These compounds can also be applied to plants and other materials in conjunction with inert solid adjuvants or carriers such as talc, pyrophyllite, attapulgite, chalk, diatomaceous earth, koalinite, montmorillonite, other silicates, silica, lime, calcium carbonate, certain organic carriers such as walnut shell flour, wood flour, ground corn cobs, and the like.

It is often desirable to use a surfactant (a surface active agent) in pesticidal compositions. An anionic, monionic or cationic surfactant can be used in the formulation of either solid or liquid compositions. Typical surfactants include alkyl sulfonates, alkylaryl sulfonates, alkyl sulfates, alkylamide sulfonates, alkylaryl polyether alcohols, fatty acid esters of polyhydric alcohols, ethylene oxide addition products of these esters; ethylene oxide addition products of long-chain mercaptans; sodium alkyl benzene sulfonates having 12 to 18 carbon atoms; ethylene oxide addition products of alkylphenols, such as phenol condensed with 10 moles of ethylene oxide; cetyl pyridinium chloride; soaps such as sodium stearate and sodium oleate.

Solid and liquid formulations can be prepared by any suitable method. Solid active ingredients, in finely divided form, can be tumbled together with a finely divided solid carrier. Alternatively, the active ingredient in liquid forms such as solutions, dispersions, emulsions or suspensions, can be admixed with the solid carrier in finely divided form in amounts small enough to preserve the free-flowing property of the final dust compositions.

When solid formulations are used, in order to obtain a high degree of coverage with a minimum dosage, it is desirable that the formulation be in the form of a finely divided powder or dust sufficiently fine that substantially all of the solids will pass through a Tyler sieve having a mesh size between about 20 and about 200.

In dust formulations, the active ingredient can be present in an amount of 5 to 50% of the total weight.

However, concentrations outside this range are operative and compositions containing from 1 to 99% of active ingredient by weight are contemplated wherein the remainder is carrier and/or any other desired additive or adjuvant. It may be advantageous to add a small amount of surfactant, e.g., 0.5 to 1% by weight based on the total weight of the dust formulation.

For spray application, the active ingredient may be dissolved or dispersed in a liquid carrier, such as water or other suitable liquid. The active ingredient can be added in the form of a solution, suspension, dispersion or emulsion in aqueous or nonaqueous medium. Desirably, 0.5 to 1.0% by weight of surfactant is present in the liquid composition.

For adjuvant purposes, any desired quantity of surfactant may be employed, such as up to 250% by weight of the active ingredient. If the surfactant is used only to impart wetting qualities to a spray solution, as little as 0.05% or less, by weight of the surfactant need be used. Larger quantities of surfactant are used because of biological behavior of the surfactant rather than its wetting properties. These considerations are particularly important in the treatment of plants. The active ingredient in liquid formulations often may not be more than 30% by weight of the total and may be 10% by weight or even as low as 0.01% by weight.

For systemic application, it may be desirable to apply the pesticide to the soil in the form of granules of an inert material coated with or incorporating the active ingredient. Reasons for the use of pesticidal granules include elimination of water during application, reduction of drift, penetration through vegetative coverage, easy handling, storage, and increased safety to handlers of the pesticides. Useful granule base materials include attapulgite, montmorillonite, corn cobs, walnut shells, and expanded vermiculites. Depending on their physical properties, the pesticides are either directly sprayed on the preformed granular base or are dissolved in a suitable solvent and then sprayed onto the granular base after which the solvent is removed by evaporation. Granule base materials are usually 60 to 14 U.S. sieve size particles, although other size particles may also be used.

Terms "pesticide" and "pesticidal" as used herein are intended to refer to the killing and/or control of insects, mites, nematodes, or the like. It will be appreciated that application commonly referred to as insecticidal, miticidal, nematocidal, or the like are contemplated in the employment of these terms.

For a fuller understanding of the nature and objects of this invention, reference may be made to the following examples which are given to illustrate the invention and are not to be construed in a limiting sense. The infrared spectrum for each product described herein is consistent with the assigned structure. All percentages, proportions, and quantities given in these examples are by weight unless otherwise indicated. Likewise, all references to temperature are as ° C. unless otherwise indicated.

EXAMPLE 1

3,3-Dimethyl-1-tert.-butylthio-2-butanone (Compound 7569)

To a solution of 5.8 g (0.25 mol) of sodium metal in 175 ml of absolute ethanol is added, dropwise, 24.4 g (0.27 mol) of 2-methyl-2-propanethiol. The stirred solution is heated for 20 minutes, cooled, and treated in a dropwise manner with 44.8 g (0.25 mol) of 1-bromopinacolone, prepared according to the procedure of J. Am Chem Soc., 74, 4507 (1952). This reaction mixture is heated at reflux for 20 minutes, cooled, and poured onto 200 g of ice and water. After being saturated with sodium chloride, the mixture is extracted with four portions of ether. The combined ether extracts are dried over anhydrous magnesium sulfate, filtered, and stripped of solvent. Distillation of the residue through a short Vigreaux column gives the desired product. Properties of this, and similar compounds prepared by substantially the same procedure using the appropriate mercaptans and haloketones, are given in Table 1.

EXAMPLE 2

3,3-Dimethyl-1-tert.-butylthio-2-butanone oxime (Compound 7604)

A solution of 27 g (0.14 mol) of 3,3-dimethyl-1-tert.-butylthio-2-butanone, 19.5 g (0.28 mol) of hydroxylamine hydrochloride and 14.8 g (0.14 mol) of anhydrous sodium carbonate in a mixture of 200 ml of 95% ethanol and 110 ml of water is heated at reflux for 19.5 hours. Stripping of volatiles on a rotary evaporator gives a slurry which is filtered to obtain the white solid oxime product. Properties of this and related compounds prepared by substantially the same procedure are given in Table 2. Where the oxime product is a liquid, isolation is accomplished by ethyl acetate extraction of the residue left after removal of the volatiles and subsequent stripping of the dried extract.

EXAMPLE 3

Carbamate Preparation—Method A 3,3-Dimethyl-2-methylcarbamyloximino-1-tert.-butylthiobutane (Compound 7619)

A solution of 4.7 g (0.023 mol) of 3,3-dimethyl-1-tert.-butylthio-2-butanone oxime, 1.4 g (0.025 mol) of methyl isocyanate, and three drops of triethylamine in 35 ml of anhydrous ether is heated at reflux for 16.5 hours. Stripping of volatiles on a rotary evaporator gives the desired product as a white solid. Properties of this and analogous compounds prepared by substantially the same procedure are given in Table 3.

EXAMPLE 4

Carbamate Preparation—Method B

2-Carbamyloximino-3,3-dimethyl-1-methylthiobutane (Compound 7859)

To a chilled solution of 5.4 g (0.055 mol) of phosgene in 50 ml of anhydrous ether is added, dropwise, 6.1 g (0.05 mol) of N,N-dimethylaniline followed by a solution of 8.1 g (0.05 mol) of 3,3-dimethyl-1-methylthio-2-butanone oxime in 50 ml of ether. The mixture is stirred for two hours, as it is allowed to come to room temperature, and then filtered. The chilled filtrate is treated over 15 minutes with 10 ml 0.15 mol) of 29% aqueous ammonia. After being stirred for additional 15 minutes, the organic layer is separated, washed with water, and dried. Stripping of solvent from the dried organic layer gives 10.1 g of a clear liquid residue which solidifies on standing. Properties of this and analogous compounds prepared by substantially the same procedure are shown in Table 3.

EXAMPLE 5

Carbamate Preparation—Method C

3,3-Dimethyl-2-methylcarbamyloximino-1-(1-pyrrolidinyl)-butane (Compound 7870)

To a solution of 12.6 g of 1-bromo-3,3-dimethyl-2-methylcarbamyloximinobutane in 100 ml of anhydrous ether is added, dropwise, 7.8 g (0.11 mol) of pyrrolidine. The mixture is stirred at room temperature for 1 hour and at reflux for 0.5 hour, then cooled and washed with water. The ether solution is separated, dried, and stripped of solvent to give 11.8 g of amber oil which solidifies on standing to an amber solid, m. 43°–46° C. Properties of this and analogous compounds prepared by substantially the same procedure are shown in Table 3.

EXAMPLE 6

3,3-Dimethyl-2-methylcarbamyloximino-1-methylsulfonyloxybutane (Compound 9350)

A solution of 7.5 g (0.04 mol) of 1-hydroxy-3,3-dimethyl-2-methylcarbamyloximinobutane and 5.0 g (0.044 mol) of methanesulfonyl chloride in 50 ml of benzene is treated dropwise with 4.6 g (0.044 mol) of triethylamine with cooling to keep the temperature below 35° C. After the addition, the stirred mixture is heated at 35° C. for two hours and then washed with aqueous sodium bicarbonate and with water. The organic layer is dried over magnesium sulfate, filtered, stripped of volatiles to give 6.7 g (63%) of amber, viscous liquid residue, $n_D^{25}$ 1.4810.

Calc'd for $C_9H_{18}N_2O_2S$: C, 40.6%; H, 6.8%; N, 10.5%. Found: C, 41.2%; H, 6.8%; N, 10.5%.

EXAMPLE 7

3,3-dimethyl-2-methylcarbamyloximino-1-methylthiobutane (Compound 7268)

Compound No. 7268 was prepared using the following procedure:

3,3-Dimethyl-1-methylthio-2-butanone

To a solution of sodium ethoxide prepared from 7.7 g (0.33 mol) of sodium metal and 200 ml of absolute alcohol was added 19 g (0.4 mol) of methanethiol over 10 min at ±2° C. To this solution of thiomethoxide was added dropwise, over 25 min. 59 g (0.28 mol) of 1-bromo-3,3-dimethyl-2-butanone prepared according to the procedure of J. Am. Chem. Soc. 74, 4507 (1952). The temperature was maintained at 0±3° C. during the addition and for a further 30 min. The reaction mixture was filtered and the solvent removed by distillation. Vacuum distillation of the residue gave the desired product as a colorless liquid, b. 73° C./9.3 mm Hg, $n_D^{24}$ 1.4650 in 54% pure yield.

3,3-Dimethyl-1-methylthio-2-butanone oxime

A solution of 20.4 g (0.14 mol) of 3,3-dimethyl-1-methylthio-2-butanone, 19.6 g (0.28 mol) of hydroxylamine hydrochloride and 14.8 g (0.14 mol) of anhydrous sodium carbonate in 140 ml of 95% ethanol and 80 ml of water was heated at reflux for 16 hr. The resulting nearly colorless solution was stripped of volatiles on a rotary evaporator to yield a two layered liquid residue. This residue was extracted with four portions of ethyl acetate. The organic extract was dried over magnesium sulfate, filtered from the drying agent and stripped of solvent. Distillation of the residue gave the desired product as a colorless liquid, b. 83° C./0.6 mm Hg, $n_D^{22}$ 1.4989.

Calc'd for $C_7H_{15}NOS$: C, 52.1; H, 9.4; N, 8.7. Found: C, 52.2; H, 9.4; N, 8.6.

3,3-Dimethyl-2-methlcarbamyloximino-1-methylthiobutane

A solution of 110 g (0.68 mol) of 3, 3-dimethyl-1-methlthio-2-butane oxime, 42.8 g (0.75 mol) of methyl isocyanate and three drops of triethylamine in 400 ml of anhydrous acetone was heated at reflux for 16 hr. Volatiles were removed by stripping on a rotary evaporator to give 155 g of white solid residue, m 50°–53° C. A solution of 25 g of this residue in 200 ml of ether was washed with two 100 ml portions of water. The dried ether solution was reduced in volume to yield 12.6 g of white crystals, m 56.5°–57.5° C., which is the desired compound.

Calc'd for $C_9H_{18}N_2O_2S$: C, 49.5; H, 8.3; N, 13.0. Found: C, 49.3; H, 8.9; N, 12.9.

In general, the sulfide compounds of the present invention will be oxidized, in situ during use, to the corresponding sulfoxide and then to the corresponding sulfone. The oxidation can also be achieved by direct synthesis, as illustrated by Example 8.

EXAMPLE 8

3,3-Dimethyl-2-methylcarbamyloximino-1-methylsulfinylbutane (Compound 7804)

A stirred mixture of 9.0 g (0.042 mol) of sodium metaperiodate in 60 ml of water and 25 ml of methanol is cooled to 0° C. as 8.8 g (0.04 mol) of 3,3-dimethyl-2-methylcarbamyloximino-1-methylthiobutane (compound 7268—Example 7) is added in portions. After stirring a 0°–10° C. for 18 hours, the mixture is allowed to warm to room temperature and stripped of volatiles on a rotary evaporator to give a residue which is extracted with ethyl acetate. The dried extract is stripped to leave 9 g (96%) of viscous yellow oil, the desired compound.

Calc'd for $C_9H_{18}N_2O_3S$: C, 46.1%; H, 7.7%. Found: C, 45.2%; H, 7.5%.

TABLE 1

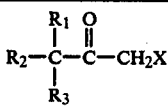

| | | | | | | | Analysis | |
| Compound Number | $R_1$ | $R_2$ | $R_3$ | X | Boiling Range in °C./mm Hg | Refractive Index/°C. | Percent Yield | Calculated | Found |
| --- | --- | --- | --- | --- | --- | --- | --- | --- | --- |
| 7218 | $CH_3-$ | $CH_3-$ | $CH_3-$ | $CH_3S-$ | 73/9.3 | 1.4650/24 | 62 | | |
| 7443 | $CH_3-$ | $CH_3-$ | $CH_3-$ | $CH_3OCOCH_2S-$ | 94/0.8 | 1.4720/24 | 64 | C 52.9  H 7.9 | C 52.6  H 7.5 |
| 7569 | $CH_3-$ | $CH_3-$ | $CH_3-$ | $(CH_3)_3CS-$ | 84–92/9.8 | 1.4595/24 | 67 | C 63.8  H 10.7 | C 63.6  H 10.6 |

TABLE 1-continued $$R_2-\underset{\underset{R_3}{|}}{\overset{\overset{R_1}{|}}{C}}-\overset{\overset{O}{\|}}{C}-CH_2X$$

| Compound Number | $R_1$ | $R_2$ | $R_3$ | X | Boiling Range in °C./mm Hg | Refractive Index/°C. | Percent Yield | Analysis Calculated | | Found | |
|---|---|---|---|---|---|---|---|---|---|---|---|
| 7573 | $CH_3-$ | $CH_3-$ | $CH_3-$ | $CH_2=CHCH_2S-$ | 58-9/1.2 | 1.4762/24 | 24 | C | 62.7 | C | 62.8 |
| | | | | | | | | H | 9.4 | H | 9.1 |
| 7637 | $CH_3-$ | $CH_3-$ | $CH_3-$ | $C_6H_5CH_2S-$ | 104.5-106/0.5-0.6 | 1.5306/24 | 57 | C | 70.2 | C | 70.9 |
| | | | | | | | | H | 8.2 | H | 9.0 |
| 7665 | $CH_3-$ | $CH_3-$ | $CH_3-$ | $C_6H_5S-$ | 102/0.5 | 1.5425/24 | 38 | C | 69.2 | C | 70.0 |
| | | | | | | | | H | 7.7 | H | 7.7 |
| 7667 | $CH_3-$ | $CH_3-$ | $CH_3S-$ | $CH_3S-$ | 91-5/3.9 | 1.5138/23 | 56 | C | 47.2 | C | 46.8 |
| | | | | | | | | H | 7.9 | H | 7.8 |
| 7765[a] | $CH_3-$ | $CH_3-$ | $CH_3-$ | $C_6H_5O-$ | 106-8/1.8 | 1.5036/23 | 72 | — | | — | |
| 7838 | $CH_3-$ | $CH_3-$ | $CH_3-$ | $CH_3CH_2CH_2S-$ | 49/0.3 | 1.4617/24 | 50 | C | 62.0 | C | 61.7 |
| | | | | | | | | H | 10.4 | H | 10.3 |
| 8126 | $-(CH_2)_5-$ | | $CH_3-$ | $CH_3S-$ | 86-7/0.8 | 1.4954/24 | 29 | C | 64.5 | C | 64.0 |
| | | | | | | | | H | 9.6 | H | 9.6 |
| 8373 | $-(CH_2)_2-$ | | $H-$ | $CH_3S-$ | 71-4/7.8 | 1.4980/22.5 | 71 | C | 55.4 | C | 55.6 |
| | | | | | | | | H | 7.7 | H | 7.9 |
| 8504 | $(CH_3)_3C-$ | $H-$ | $H-$ | $CH_3S-$ | 68/4.8 | 1.4600/22 | 66 | C | 59.9 | C | 59.0 |
| | | | | | | | | H | 10.0 | H | 9.8 |
| 9011 | $(CH_3)_2CH-$ | $H-$ | $H-$ | $CH_3S-$ | 81/9.3 | 1.4610/23 | 76 | (b) | | | |
| 9275 | $CH_3-$ | $CH_3-$ | $CH_3-$ | $CH_3CH_2SCH_2CH_2S-$ | 110/0.3 | 1.5025/24 | 65 | C | 54.8 | C | 54.6 |
| | | | | | | | | H | 8.7 | H | 9.2 |
| 9278[c] | $CH_3-$ | $CH_3-$ | $CH_3-$ | $CH_3O-$ | 78/47 | 1.4136/23 | 57 | C | 64.5 | C | 64.3 |
| | | | | | | | | H | 10.8 | H | 10.8 |
| 9380 | $CH_3-$ | $CH_3-$ | $CH_3-$ | $CF_3CH_2CH_2S-$ | 60/0.08 | 1.4253/24 | 40 | C | 47.4 | C | 47.6 |
| | | | | | | | | H | 6.6 | H | 6.6 |
| 9382 | $CH_3-$ | $CH_3-$ | $CH_3-$ | $Cl_3CCH_2CH_2S-$ | 113/0.1 | 1.5055/24 | 39 | C | 40.0 | C | 40.2 |
| | | | | | | | | H | 5.4 | H | 5.5 |
| 9385 | $CH_3-$ | $CH_3-$ | $CH_3-$ | $HC\equiv CCH_2S-$ | 72/0.08 | 1.5112/24 | 14 | C | 63.5 | C | 63.3 |
| | | | | | | | | H | 8.2 | H | 8.2 |

[a] J. Am. Chem. Soc., 77, 3272 (1955)
[b] Ann. 672, 156 (1964)
[c] J. Am. Chem. Soc., 72, 5161 (1950)

TABLE 2

$$R_2-\underset{\underset{R_3}{|}}{\overset{\overset{R_1}{|}}{C}}-\overset{\overset{NOH}{\|}}{C}-CH_2X$$

| Compound Number | $R_1$ | $R_2$ | $R_3$ | X | Melting Point in °C. | Percent Yield | Analysis Calculated | | Found | |
|---|---|---|---|---|---|---|---|---|---|---|
| 7252 | $CH_3-$ | $CH_3-$ | $CH_3-$ | $CH_3S-$ | (a) | 92 | — | | — | |
| 7470 | $CH_3-$ | $CH_3-$ | $CH_3-$ | $CH_3OCOCH_2S-$ | — | 87 | C | 49.3 | C | 49.4 |
| | | | | | | | H | 7.7 | H | 7.7 |
| | | | | | | | N | 6.4 | N | 6.2 |
| 7604 | $CH_3-$ | $CH_3-$ | $CH_3-$ | $(CH_3)_3CS-$ | 120-121 | 75 | C | 59.1 | C | 59.1 |
| | | | | | | | H | 10.4 | H | 10.4 |
| 7605 | $CH_3-$ | $CH_3-$ | $CH_3-$ | $(CH_3)_2CHS-$ | 51-52 | 63 | C | 57.1 | C | 56.5 |
| | | | | | | | H | 10.1 | H | 9.5 |
| 7618 | $CH_3-$ | $CH_3-$ | $CH_3-$ | $(CH_3)_2CHCH_2S-$ | (b) | 38 | C | 59.1 | C | 59.2 |
| | | | | | | | H | 10.4 | H | 10.5 |
| 7682 | $CH_3-$ | $CH_3-$ | $CH_3-$ | $C_6H_5CH_2S-$ | 84-87 | 100 | C | 65.8 | C | 65.6 |
| | | | | | | | H | 8.1 | H | 9.2 |
| 7711 | $CH_3-$ | $CH_3-$ | $CH_3-$ | $C_6H_5S-$ | 83-84 | 29 | C | 64.5 | C | 64.1 |
| | | | | | | | H | 7.7 | H | 8.0 |
| 7796 | $CH_3-$ | $CH_3-$ | $CH_3-$ | $C_6H_5O-$ | 104-105 | 83 | C | 69.5 | C | 70.1 |
| | | | | | | | H | 8.3 | H | 8.3 |
| | | | | | | | N | 6.8 | N | 6.9 |
| 7898 | $CH_3-$ | $CH_3-$ | $CH_3-$ | $CH_2=CHCH_2S-$ | 57-58 | 56 | N | 7.5 | N | 7.3 |
| 7925 | $CH_3CH_2CH_2-$ | $CH_3-$ | $CH_3-$ | $CH_3S-$ | (c) | — | N | 7.4 | N | 7.4 |
| 7946 | $CH_3S-$ | $CH_3-$ | $CH_3-$ | $CH_3S-$ | 70-75 | 75 | C | 43.5 | C | 42.8 |
| | | | | | | | N | 7.8 | N | 7.8 |
| 8154 | $-(CH_2)_5-$ | | $CH_3-$ | $CH_3S-$ | (d) | 63 | C | 59.7 | C | 59.8 |
| | | | | | | | H | 9.5 | H | 9.5 |
| | | | | | | | N | 7.0 | N | 7.0 |
| 8420 | $-(CH_2)_2-$ | | $H-$ | $CH_3S-$ | (e) | 95 | N | 9.7 | N | 9.5 |
| 8872 | $CH_3-$ | $CH_3-$ | $CH_3-$ | $CH_3SO_2-$ | 73-75 | 40 | N | 7.3 | N | 7.2 |
| 8873 | $CH_3-$ | $CH_3-$ | $CH_3-$ | $CH_3S(O)-$ | 104-106 | 35 | C | 47.4 | C | 47.3 |
| | | | | | | | H | 8.5 | H | 8.3 |
| | | | | | | | N | 7.9 | N | 7.9 |
| 9301 | $CH_3-$ | $CH_3-$ | $CH_3-$ | $CH_3O-$ | (f) | 45 | C | 57.9 | C | 57.6 |
| | | | | | | | H | 10.4 | H | 9.9 |
| 9302 | $CH_3-$ | $CH_3-$ | $CH_3-$ | $CH_3CH_2O-$ | (g) | 74 | N | 8.8 | N | 8.6 |
| 9332 | $CH_3-$ | $CH_3-$ | $CH_3-$ | $CH_3CH_2SCH_2CH_2S-$ | 42-45 | 81 | C | 51.1 | C | 51.1 |

TABLE 2-continued $$R_2-\underset{\underset{R_3}{|}}{\overset{\overset{R_1}{|}}{C}}-\overset{\overset{NOH}{\parallel}}{C}-CH_2X$$

| Compound Number | $R_1$ | $R_2$ | $R_3$ | X | Melting Point in °C. | Percent Yield | Analysis Calculated | | Found | |
|---|---|---|---|---|---|---|---|---|---|---|
| | | | | | | | H 9.0 | | H 8.9 | |
| | | | | | | | N 6.0 | | N 5.8 | |
| 9381 | $CH_3-$ | $CH_3-$ | $CH_3-$ | $F_3CCH_2CH_2S-$ | 41–43 | 89 | C 44.4 | | C 45.0 | |
| | | | | | | | H 6.6 | | H 6.7 | |
| 9384 | $CH_3-$ | $CH_3-$ | $CH_3-$ | $C_6H_5CH_2CH_2S-$ | 48–50 | 98 | C 66.9 | | C 67.8 | |
| | | | | | | | H 8.4 | | H 8.5 | |
| 9430 | $CH_3-$ | $CH_3-$ | $CH_3-$ | $-SCH_2CH_2CCl_3$ | 77–80 | 61 | C 37.0 | | C 37.7 | |
| | | | | | | | H 5.5 | | H 5.4 | |
| | | | | | | | N 4.8 | | N 4.5 | |
| 9434 | $CH_3-$ | $CH_3-$ | $CH_3-$ | $-SCH_2C\equiv CH$ | (1.5260/24) | 31 | C 58.4 | | C 57.1 | |
| | | | | | | | H 8.1 | | H 8.2 | |
| | | | | | | | N 7.6 | | N 7.8 | |
| 9876 | $CH_3-$ | $CH_3-$ | $CH_3-$ |  | 98–100 | 76 | C 58.9 | | C 58.3 | |
| | | | | | | | H 7.2 | | H 7.3 | |
| | | | | | | | N 12.5 | | N 12.4 | |
| 10567 | $CH_3-$ | $CH_3-$ | $CH_3-$ |  | 125–126.5 | 57 | C 58.9 | | C 58.9 | |
| | | | | | | | H 7.2 | | H 7.2 | |
| | | | | | | | N 12.5 | | N 12.8 | |

(a) $n_D^{25}$ 1.4965
(b) b. 104° C./0.8 mm
(c) $n_D^{24}$ 1.4863
(d) $n_D^{24}$ 1.5164
(e) $n_D^{23}$ 1.5340
(f) $n_D^{24}$ 1.4460
(g) $n_D^{24}$ 1.4420

TABLE 3

$$R_2-\underset{\underset{R_3}{|}}{\overset{\overset{R_1}{|}}{C}}-\overset{\overset{NOCN\underset{R_7}{\overset{R_6}{<}}}{\parallel}}{C}-CH_2X$$

| Compound No. | $R_1$ | $R_2$ | $R_3$ | $R_6$ | $R_7$ | X | Method* | Melting Point in °C. (Refractive Index/°C.) | Analysis Calc. | Found |
|---|---|---|---|---|---|---|---|---|---|---|
| 7268 | $CH_3-$ | $CH_3-$ | $CH_3-$ | $CH_3-$ | $H-$ | $CH_3S-$ | A | 50–52 | C 49.5 H 8.3 N 13.0 | C 49.3 H 8.9 N 12.9 |
| 7472(a) | $CH_3-$ | $CH_3-$ | $CH_3-$ | $CH_3-$ | $H-$ | $H-$ | A | 45–46 | C 55.8 H 9.4 | C 55.8 H 9.1 |
| 7503 | $CH_3-$ | $CH_3-$ | $CH_3-$ | $CH_3-$ | $H-$ | $H_3COCOCH_2S-$ | A | (1.5016/23.5) | C 47.8 H 7.3 | C 48.0 H 7.6 |
| 7577(a) | $CH_3-$ | $CH_3-$ | $CH_3S-$ | $CH_3-$ | $H-$ | $H-$ | A | 79 | — | — |
| 7619 | $CH_3-$ | $CH_3-$ | $CH_3-$ | $CH_3-$ | $H-$ | $(CH_3)_3CS-$ | A | 105–106 | C 55.3 H 9.3 | C 55.1 H 9.3 |
| 7620 | $CH_3-$ | $CH_3-$ | $CH_3-$ | $CH_3-$ | $H-$ | $(CH_3)_2CHS-$ | A | 63–64 | C 53.6 H 9.0 | C 53.6 H 8.5 |
| 7639 | $CH_3-$ | $CH_3-$ | $CH_3-$ | $CH_3-$ | $H-$ | $(CH_3)_2CHCH_2S-$ | A | 66–67 | C 55.3 H 9.3 | C 55.2 H 9.5 |
| 7702 | $CH_3-$ | $CH_3-$ | $CH_3-$ | $CH_3-$ | $H-$ | $C_6H_5CH_2S-$ | A | 54–56 | C 61.2 H 7.5 | C 61.1 H 7.5 |
| 7718 | $CH_3-$ | $CH_3-$ | $CH_3-$ | $CH_3-$ | $H-$ | $C_6H_5S-$ | A | 106–107 | C 60.0 H 7.2 | C 60.0 H 7.4 |
| 7797 | $CH_3-$ | $CH_3-$ | $CH_3-$ | $CH_3CH_2-$ | $H-$ | $CH_3S-$ | A | (1.4941/24) | C 51.7 H 8.7 N 12.1 | C 51.1 H 8.5 N 11.6 |
| 7799 | $CH_3-$ | $CH_3-$ | $CH_3-$ | $CH_2=CHCH_2-$ | $H-$ | $CH_3S-$ | A | (1.5017/24) | C 54.1 H 8.3 N 11.5 | C 53.5 H 8.0 N 11.2 |
| 7803 | $CH_3-$ | $CH_3-$ | $CH_3-$ | $CH_3-$ | $H-$ | $C_6H_5O-$ | A | 128–129 | C 63.6 H 7.6 N 10.6 | C 63.7 H 7.7 N 10.7 |
| 7804 | $CH_3-$ | $CH_3-$ | $CH_3-$ | $CH_3-$ | $H-$ | $CH_3S(O)-$ | D | (1.5040/24) | C 46.1 H 7.7 N 12.0 | C 45.2 H 7.5 N 11.9 |
| 7859 | $CH_3-$ | $CH_3-$ | $CH_3-$ | $H-$ | $H-$ | $CH_3S-$ | B | 58–60 | C 47.0 | C 46.7 |

TABLE 3-continued $$\underset{R_2-\underset{R_3}{\overset{R_1}{C}}-C=C-CH_2X}{NOCN\underset{R_7}{\overset{O}{\overset{\parallel}{\underset{R_6}{\nearrow}}}}}$$

| Compound No. | R₁ | R₂ | R₃ | R₆ | R₇ | X | Method* | Melting Point in °C. (Refractive Index/°C.) | Analysis Calc. | Found |
|---|---|---|---|---|---|---|---|---|---|---|
| 7870 | CH₃— | CH₃— | CH₃— | CH₃— | H— | C₄H₈N—⁽ᵇ⁾ | C | 43–46 | H 7.9<br>N 13.7<br>N 17.4 | H 7.7<br>N 13.5<br>N 17.0 |
| 7895 | CH₃— | CH₃— | CH₃— | CH₃— | H— | CH₃NHCOO— | A | (1.4796/24) | C 49.0<br>H 7.8 | C 49.7<br>H 7.8 |
| 7897 | CH₃— | CH₃— | CH₃— | CH₃— | H— | CH₂=CHCH₂S— | A | (1.5075/25) | N 11.5 | N 11.9 |
| 7934 | CH₃CH₂CH₂— | CH₃— | CH₃— | CH₃— | H— | CH₃S— | A | (1.4937/24) | C 53.8<br>H 9.0<br>N 11.4 | C 53.2<br>H 8.8<br>N 11.5 |
| 7960 | CH₃S— | CH₃— | CH₃— | CH₃— | H— | CH₃S— | A | (1.5339/24) | C 43.2<br>H 7.2<br>N 11.2 | C 43.7<br>H 7.2<br>N 11.7 |
| 7991 | CH₃— | CH₃— | CH₃— | CH₃— | H— | NCS— | C | 85–86 | C 47.1<br>H 6.6<br>N 18.3 | C 47.5<br>H 6.6<br>N 18.8 |
| 8018 | CH₃— | CH₃— | CH₃— | CH₃— | H— | C₆H₁₁S— | C | 105–106 | C 58.7<br>H 9.2<br>N 9.8 | C 59.1<br>H 9.1<br>N 9.8 |
| 8031 | CH₃— | CH₃— | CH₃— | CH₃— | H— | CH₃COO— | C | 48–50 | C 52.1<br>H 7.9<br>N 12.2 | C 51.8<br>H 7.8<br>N 12.4 |
| 8036 | CH₃— | CH₃— | CH₃— | CH₃— | H— | 4-(CH₃)₃CC₆H₄S— | C | (1.5348/24) | C 64.2<br>H 8.4<br>N 8.3 | C 64.7<br>H 8.4<br>N 8.4 |
| 8070 | CH₃— | CH₃— | CH₃— | CH₃ | H— | 4-CH₃OC₆H₄S— | C | 90–92 | C 58.0<br>H 7.2<br>N 9.0 | C 57.6<br>H 7.0<br>N 8.7 |
| 8073 | CH₃— | CH₃— | CH₃— | CH₃— | H— | 4-ClC₆H₄S— | C | 111–112 | C 53.4<br>H 6.1<br>N 8.9 | C 53.0<br>H 6.1<br>N 8.9 |
| 8169 | —(CH₂)₅— | | H— | CH₃— | H— | CH₃S— | A | 70–71 | C 54.1<br>H 8.3<br>N 11.5 | C 54.2<br>H 8.3<br>N 11.8 |
| 8179 | —(CH₂)₅— | | CH₃— | CH₃— | H— | CH₃S— | A | (1.5200/25) | C 55.8<br>H 8.6 | C 55.7<br>H 8.6 |
| 8465 | —(CH₂)₂— | | H— | CH₃— | H— | CH₃S— | A | (1.5297/23) | N 13.9 | N 14.3 |
| 8519 | (CH₃)₃C— | H— | H— | CH₃— | H— | CH₃S— | A | (1.4960/23) | C 51.7<br>H 8.7 | C 51.3<br>H 8.5 |
| 8813 | —(CH₂)₂— | | H— | CH₃CH₂— | H— | CH₃S— | A | (1.5205/24) | C 50.0<br>H 7.5<br>N 12.3 | C 49.8<br>H 7.3<br>N 12.2 |
| 8814 | —(CH₂)₂— | | H— | CH₂=CHCH₂— | H— | CH₃S— | A | (1.5296/24) | | |
| 8868 | CH₃— | CH₃— | CH₃— | CH₃— | H— | CH₃SO₂— | A | (1.4923/22) | N 11.2 | N 11.1 |
| 9026 | CH₃— | CH₃— | CH₃— | CH₃— | H— | CH₃SCH₂CH₂S— | C | 51–56 | C 47.5<br>H 8.0 | C 47.5<br>H 8.0 |
| 9058 | (CH₃)₂CH— | H— | H— | CH₃— | H— | CH₃S— | A | (1.5005/24) | C 49.5<br>H 8.3<br>N 12.8 | C 49.4<br>H 8.4<br>N 12.7 |
| 9071 | (CH₃)₂CH— | H— | H— | CH₂=CHCH₂— | H— | CH₃S— | A | (1.5035/23) | C 54.1<br>H 8.3<br>N 11.5 | C 54.1<br>H 8.3<br>N 11.3 |
| 9072 | CH₃CH₂— | H— | H— | CH₂=CHCH₂— | H— | CH₃S— | A | (1.5070/23) | N 12.2 | N 12.3 |
| 9226 | CH₃— | CH₃— | CH₃— | CH₂=CHCH₂— | H— | CH₃SCH₂CH₂S— | A | (1.5285/24) | C 51.4<br>H 7.9<br>N 9.2 | C 51.4<br>H 7.8<br>N 9.4 |
| 9300 | CH₃— | CH₃— | CH₃— | CH₃— | H— | CH₃O— | A | (1.4650/24) | C 53.4<br>H 9.0 | C 52.8<br>H 9.0 |
| 9315 | CH₃— | CH₃— | CH₃— | CH₃— | H— | CH₃CH₂O— | A | (1.4649/24) | N 13.0 | N 13.4 |
| 9337 | CH₃— | CH₃— | CH₃— | CH₃— | H— | CH₃CH₂SCH₂CH₂S— | A | (1.5261/23) | C 49.3<br>H 8.3 | C 49.8<br>H 8.3 |
| 9350 | CH₃— | CH₃— | CH₃— | CH₃— | H— | CH₃SO₃— | E | (1.4810/25) | C 40.6<br>H 6.8<br>N 10.5 | C 41.2<br>H 6.8<br>N 10.5 |
| 9386 | CH₃— | CH₃— | CH₃— | CH₃— | H— | F₃CCH₂CH₂S— | A | 64–66 | C 44.0<br>H 6.3 | C 44.2<br>H 6.5 |
| 9387 | CH₃— | CH₃— | CH₃— | CH₃CH₂— | H— | F₃CCH₂CH₂S— | A | (1.4623/24) | C 45.9<br>H 6.7<br>N 8.9 | C 46.7<br>H 6.9<br>N 9.0 |
| 9388 | CH₃— | CH₃— | CH₃— | CH₂=CHCH₂— | H— | F₃CCH₂CH₂S— | A | (1.4717/24) | C 47.9<br>H 6.4<br>N 8.6 | C 48.7<br>H 6.6<br>N 9.1 |
| 9389 | CH₃— | CH₃— | CH₃— | CH₃— | H— | C₆H₅CH₂CH₂S— | A | (1.5405/24) | C 62.3 | C 62.8 |

TABLE 3-continued

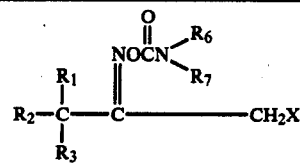

| Compound No. | R$_1$ | R$_2$ | R$_3$ | R$_6$ | R$_7$ | X | Method* | Melting Point in °C. (Refractive Index/°C.) | Analysis Calc. | Found |
|---|---|---|---|---|---|---|---|---|---|---|
| 9391 | CH$_3$— | CH$_3$— | CH$_3$— | CH$_2$=CHCH$_2$— | H— | C$_6$H$_5$CH$_2$CH$_2$S— | A | (1.4253/24) | H 8.0<br>C 64.7 | H 7.8<br>C 65.5 |
| 9425 | CH$_3$— | CH$_3$— | CH$_3$— | CH$_3$— | H— | ![phthalimide] | A | 159–160 | H 7.8<br>C 60.5<br>H 6.1<br>N 13.2 | H 8.1<br>C 60.2<br>H 6.1<br>N 13.3 |
| 9431 | CH$_3$— | CH$_3$— | CH$_3$— | CH$_3$— | H— | —SCH$_2$CH$_2$CCl$_3$ | A | 87–89 | C 37.8<br>H 5.4<br>N 8.0 | C 38.7<br>H 5.6<br>N 7.9 |
| 9432 | CH$_3$— | CH$_3$— | CH$_3$— | C$_2$H$_5$— | H— | —SCH$_2$CH$_2$CCl$_3$ | A | (1.5168/24) | C 39.7<br>H 5.8<br>N 7.7 | C 40.0<br>H 5.9<br>N 7.9 |
| 9433 | CH$_3$— | CH$_3$— | CH$_3$— | CH$_2$=CHCH$_2$— | H— | —SCH$_2$CH$_2$CCl$_3$ | A | (1.5228/24) | C 41.6<br>H 5.6 | C 42.8<br>H 5.6 |
| 9435 | CH$_3$— | CH$_3$— | CH$_3$— | CH$_3$— | H— | —SCH$_2$C≡CH | A | 64–66 | C 54.7<br>H 7.4<br>N 11.6 | C 53.3<br>H 7.6<br>N 12.1 |
| 9542 | CH$_3$— | CH$_3$— | CH$_3$— | CH$_3$— | H— | —SCH$_2$-(thienyl) | A | (1.5542/24) | C 52.0<br>H 6.7 | C 52.0<br>H 6.7 |
| 9543 | CH$_3$— | CH$_3$— | CH$_3$— | CH$_3$— | H— | —SCH$_2$-(thienyl) | A | (1.5480/24) | C 53.5<br>H 7.0 | C 53.6<br>H 6.9 |
| 9544 | CH$_3$— | CH$_3$— | CH$_3$— | H$_2$C=CHCH$_2$— | H— | —SCH$_2$-(thienyl) | A | (1.5507/24) | C 55.2<br>H 6.8 | C 55.7<br>H 6.8 |
| 9901 | CH$_3$— | CH$_3$— | CH$_3$— | CH$_3$— | H— | —S-(2-pyridyl) | A | 80–83 | C 55.5<br>H 6.8<br>N 14.9 | C 54.7<br>H 6.9<br>N 15.2 |
| 9902 | CH$_3$— | CH$_3$— | CH$_3$— | C$_2$H$_5$— | H— | —S-(2-pyridyl) | A | 92–94 | C 56.9<br>H 7.2<br>N 14.2 | C 56.6<br>H 7.4<br>N 14.3 |
| 9903 | CH$_3$— | CH$_3$— | CH$_3$— | H$_2$C=CHCH$_2$— | H— | —S-(2-pyridyl) | A | 54–56 | C 58.6<br>H 6.9<br>N 13.7 | C 58.1<br>H 7.0<br>N 14.0 |
| 10629 | CH$_3$— | CH$_3$— | CH$_3$— | CH$_2$=CHCH$_2$— | H— | —S-(4-pyridyl) | A | 118–119 | C 58.6<br>H 6.9<br>N 13.7 | C 59.1<br>H 7.1<br>N 13.5 |
| 10673 | CH$_3$— | CH$_3$— | CH$_3$— | CH$_3$— | H— | N-(pyridyl)S— | A | 140–142 | C 55.5<br>H 6.9<br>N 14.9 | C 55.1<br>H 6.9<br>N 15.6 |
| 10879 | CH$_3$— | CH$_3$— | CH$_3$— | CH$_3$— | H— | SCN(CH$_3$)$_2$—<br>‖<br>S | C | 148–150 | C 45.3<br>H 7.3<br>N 14.4 | C 45.0<br>H 7.3<br>N 14.1 |
| 10987 | CH$_3$— | CH$_3$— | CH$_3$— | CH$_3$— | H— | —S-thiazolyl-C(CH$_3$)$_3$ | C | 149 | C 42.5<br>H 6.2<br>N 9.9 | C 42.5<br>H 6.2<br>N 10.1 |
| 11575 | CH$_3$— | CH$_3$— | CH$_3$— | CH$_3$— | H— | —S-(pyrimidinyl) | C | 110–111 | C 51.0<br>H 6.4<br>N 19.8 | C 51.3<br>H 6.6<br>N 20.8 |

TABLE 3-continued

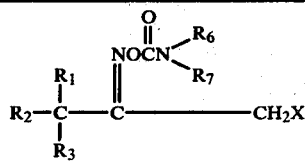

| Compound No. | R₁ | R₂ | R₃ | R₆ | R₇ | X | Method* | Melting Point in °C. (Refractive Index/°C.) | Analysis Calc. | Found |
|---|---|---|---|---|---|---|---|---|---|---|
| 11576 | CH₃— | CH₃— | CH₃— | CH₃— | H— | H₃C-pyrimidinyl-S— | C | 112–114 | C 52.7<br>H 6.8<br>N 18.9 | C 52.6<br>H 6.9<br>N 19.5 |
| 11695 | CH₃— | CH₃— | CH₃— | CH₃— | H— | thiazoline-S— | C | 76–80 | C 45.7<br>H 6.6<br>N 14.5 | C 44.9<br>H 6.6<br>N 14.1 |
| 11696 | CH₃— | CH₃— | CH₃— | CH₃— | H— | pyridyl-SO₂— | E | 105–107 | C 49.8<br>H 6.1<br>N 13.4 | C 49.5<br>H 6.2<br>N 13.7 |
| 11806 | CH₃— | CH₃— | CH₃— | CH₃— | H— | H₃C-thiazoline-S— | C | (1.5523/24) | C 47.8<br>H 6.4<br>N 13.9 | C 47.4<br>H 6.5<br>N 13.7 |
| 11913 | CH₃— | CH₃— | CH₃— | CH₃— | H— | pyridyl-N-oxide-S— | C | 115–157 | C 52.5<br>H 6.4<br>N 14.1 | C 52.9<br>H 6.6<br>N 14.0 |
| 11949 | CH₃— | CH₃— | CH₃— | CH₃— | H— | N-CH₃-thiazoline-S— | C | (1.5430/29) | C 50.7<br>H 7.1<br>N 19.7 | C 49.7<br>H 7.2<br>N 19.8 |
| 12295 | CH₃— | CH₃— | CH₃— | CH₃— | H— | H₃C-thiadiazole-S— | C | 86–87 | C 43.7<br>H 6.0<br>N 18.5 | C 44.3<br>H 6.3<br>N 18.8 |

*Method:
A = Example 3
B = Example 4
C = Example 5
D = Example 8
E = Example 8, substituting peracetic acid for the sodium metaperiodate
(a)J. Agr. Food Chem., 14, 356 (1966)
(b)1-pyrrolidinyl
(c)hydrochloride salt The compounds are evaluated for biological activity against the following representative pests: Mexican bean beetle (*Epilachna varivestis*), Southern army worm (*Prodenia eridania*), housefly (*Musca domestica*), bean aphid (*Aphis fabae*), and red spider mite (*Tetranychus sp.*). The last two pests are treated both by contact and systemic application.

For purposes of comparison, results obtained with known Compound 7472, Compound 7577, and aldicarb are included in the test results. Each test compound is rated using the following scale:

| Contact Activity | | Systemic Activity | |
|---|---|---|---|
| Rating Number | = ≧50% mortality at concentration in parts per million of | Rating Number | = ≧50% mortality at concentration in pounds per acre of |
| 0 | 500 | 0 | 16 |
| 1 | 500–250 | 1 | 16–8 |
| 2 | 250–128 | 2 | 8–4 |
| 3 | 128–64 | 3 | 4–2 |
| 4 | 64–32 | 4 | 2–1 |
| 5 | 32–16 | 5 | 1–1/2 |
| 6 | 16–8 | 6 | 1/2–1/4 |
| 7 | 8–4 | 7 | 1/4–1/8 |
| 8 | 4–2 | 8 | 1/8–1/16 |
| 9 | 2 | 9 | 1/16 |

The tests employed are:

EXAMPLE 9

Bean Aphid Spray and Systemic Test

This test determines the insecticidal activity of the compound being tested against the bean aphid *Aphis*

*fabae*. Stock formulations containing 500 ppm of each test chemical are prepared using 0.05 g of the test chemical (or 0.05 ml of a liquid), 4.0 ml acetone containing 0.25% (V/V) Triton X-155, and 96.0 ml deionized water and are used in both soil drench and spray treatments. The stock formulations are diluted to obtain the appropriate lower concentrations maintaining the concentration level of all adjuvants. The Bean aphid is cultured on nasturtium plants (var. Tall Single), no attempt being made to select insects of a given age in these tests. Single nasturtium test plants growing in soil in individual 2¼ inch fiber pots are fested with populations of 100 to 200 aphids.

In the spray application, 50 ml of stock or diluted formulation is uniformly sprayed onto the plants. In the systemic application, 11.2 ml of stock or diluted formulation is applied to the soil containing the plant. A dosage of 11.2 ml of formulation containing 500 ppm of test chemical is equivalent to a dosage of the test chemical of 16 pounds per acre.

The plant test units under fluorescent lights are given bottom watering for the duration of the test. Percentage mortality is determined three days after treatment. Results of this test are shown in Table 4 as A (aphid contact spray) and AS (aphid systemic soil drench).

EXAMPLE 10

Red Spider Mite Spray and Systemic Test

This test determines the acaricidal activity of the compound being tested against the red spider mite, *Tetranychus* sp. Stock formulations containing 500 ppm of each test chemical are prepared by the procedure described in Example 9 and are used in both the soil drench and spray treatments. The stock culture of mites is maintained on Scarlet runner bean foliage. Approximately 18 to 24 hours before testing, mites are transferred to the primary leaves of two Lima bean plants (var. Sieva) grown in 2¼ inch pots.

The spray and systemic application methods described in Example 10 are used to apply the test formulations to the infested plants and soil. After three days, two of the four leaves treated are examined and mortality is determined. Should a compound be an effective miticide, the other two leaves are available to obtain information on the residual activity of the formulation. Results of this test are shown in Table 4 as M (mite contact spray test) and MS (mite systemic soil drench test).

EXAMPLE 11

Housefly Spray Test

This test determines the insecticidal activity of the compound being tested against adult houseflies, *Musca domestica*. Stock formulations containing 500 ppm of each test chemical are prepared using the procedure described in Example 10 and are diluted to obtain the appropriate lower concentrations.

Ten adult flies are placed in a cylindrical screen cage 1½ by 4 inches fabricated from 20-mesh stainless steel screening and are sprayed with 50 ml of the stock or diluted formulation. The flies are supplied food and drink from a dextrose solution by draping a paper wick over the outside of the screen cylinder and are able to feed and drink ad libitum. Percent mortality obtained is determined three days after treatment. Results of this test are shown in Table 4 as HF (housefly spray test).

EXAMPLE 12

Southern Army Worm Spray Test

Paired fully expanded primary leaves excised from Scarlet runner bean plants are maintained in plastic tubes containing water and sprayed with the test formulation prepared as described in Example 10. After the spray deposit on the leaves is dry, the paired leaves are separated. One leaf is placed onto 1.5 percent water agar and infested with 10 newly hatched Southern army worm larvae. The covered test receptacle is held at 72° F. for three days and then the percent mortality is determined. Results of this test are shown in Table 4 as AW (Southern army worm spray test).

EXAMPLE 13

Mexican Bean Beetle Leaf Spray Test

This test determines the insecticidal activity of the compound being tested against the Mexican bean beetle (*Epilachna varivestis*). The test procedure is the same as that described for the Southern army worm in Example 12 with the exception that one-day old larvae of the Mexican bean beetle instead of newly hatched Southern army worm larvae are used.

These tests are held at 72° F. for three days when mortality and feeding inhibition are determined. The feeding inhibition is an indication of the repellent properties of the test material. Results of this test are shown in Table 4 as BB (Mexican bean beetle leaf spray test).

TABLE 4

| Compound Number* | BB[1] | AW[2] | HF[3] | M[4] | A[5] | MS[6] | AS[7] |
| --- | --- | --- | --- | --- | --- | --- | --- |
| 7268 | 5 | 0 | 1 | 7 | 9 | 5 | 7 |
| 7472 | 0 | 0 | 0 | 0 | 1 | 0 | 1 |
| 7503 | 3 | 0 | 0 | 1 | 6 | 1 | 0 |
| 7577 | 0 | 0 | 0 | 0 | 0 | 0 | 0 |
| 7718 | 5 | 0 | 1 | 0 | 2 | 0 | 1 |
| 7797 | 2 | 0 | 3 | 3 | 5 | 3 | 4 |
| 7799 | 5 | 0 | 2 | 2 | 5 | 2 | 0 |
| 7804 | 6 | 2 | 2 | 5 | 8 | 5 | 7 |
| 7859 | 4 | 0 | 0 | 5 | 7 | 3 | 4 |
| 7897 | 4 | 0 | 3 | 4 | 4 | 1 | 3 |
| 7934 | 5 | 0 | 0 | 6 | 6 | 2 | 2 |
| 7960 | 4 | 0 | 0 | 5 | 5 | 0 | 0 |
| 7991 | 5 | 0 | 0 | 0 | 2 | 0 | 0 |
| 8465 | 4 | 1 | 2 | 2 | 5 | 0 | 4 |
| 8868 | 7 | 0 | 2 | 6 | 8 | 6 | 7 |
| 9026 | 6 | 0 | 0 | 4 | 4 | 0 | 0 |
| 9058 | 0 | 0 | 1 | 2 | 7 | 0 | 6 |
| 9425 | 0 | 0 | 0 | 0 | 0 | 0 | 0 |
| 9431 | 4 | 0 | 0 | 0 | 1 | 0 | 0 |
| 9432 | 2 | 0 | 0 | 0 | 0 | 0 | 0 |
| 9433 | 2 | 0 | 0 | 0 | 1 | 0 | 0 |
| 9435 | 3 | 2 | 3 | 3 | 4 | 1 | 3 |
| 9542 | 4 | 0 | 0 | 0 | 2 | 0 | 0 |
| 9543 | 3 | 0 | 0 | 0 | 0 | 0 | 0 |
| 9544 | 3 | 0 | 0 | 0 | 0 | 0 | 0 |
| 9901 | 5 | 0 | 2 | 4 | 6 | 0 | 0 |
| 9902 | 4 | 0 | 0 | 0 | 3 | 0 | 0 |
| 9903 | 3 | 0 | 3 | 0 | 3 | 0 | 0 |
| 10629 | 3 | 0 | 0 | 0 | 0 | 0 | 0 |
| 10673 | 5 | 0 | 3 | 0 | 3 | 0 | 3 |
| 10879 | 5 | 0 | 0 | 0 | 0 | 0 | 0 |
| 10987 | 4 | 0 | 0 | 0 | 0 | 0 | 0 |
| 11575 | 5 | 0 | 3 | 0 | 4 | 0 | 3 |
| 11576 | 4 | 0 | 0 | 0 | 3 | 0 | 3 |
| 11695 | 5 | 0 | 0 | 0 | 0 | 0 | 0 |
| 11696 | 7 | 0 | 3 | 5 | 9 | 3 | 3 |
| 11806 | 7 | 0 | 3 | 0 | 5 | 0 | 3 |
| 11913 | 4 | 0 | 0 | 0 | 3 | 0 | 3 |
| 11949 | 4 | 0 | 0 | 0 | 5 | 0 | 3 |
| 12295 | 7 | 0 | 3 | 0 | 4 | 0 | 4 |

TABLE 4-continued

| Compound Number* | BB[1] | AW[2] | HF[3] | M[4] | A[5] | MS[6] | AS[7] |
|---|---|---|---|---|---|---|---|
| aldicarb | 4 | 0 | 7 | 4 | 9 | 5 | 9 |

[1]BB = Mexican bean bettle
[2]AW = Southern army worm
[3]HF = housefly
[4]M = mite contact
[5]A = aphid contact
[6]MS = mite systemic
[7]AS = aphid systemic
*Those compound numbers which are not identified in Table 3, hereinbefore, are identified in Table 6 of USSN 229,207.

It is to be noted that Compound 7268 exhibits outstanding activity against all of the pests except the Southern army worm and the housefly. This activity is comparable or superior to that of the commercial material, aldicarb (Formula III), and vastly superior to that of Compound 7472 (Formula I), the unsubstituted 3,3-dimethyl-2-butanone derivative, or Compound 7577 (Formula II), the ketoxime analog of aldicarb.

The high insecticidal and miticidal activity of Compound 7268 is further demonstrated by the results of special tests described below.

EXAMPLE 14

Systemic Test of Compound 7268 Against Lygus Bug and Spotted Cucumber Beetle

The techniques used are essentially the same for the systemic tests described above in Example 10. The test compound is Compound 7268. There is one Sieva bean plant per pot and five adult insects are caged on each plant. One plant is used for each test species. The checks showed no mortality during the tests.

| Dosage, lb/A | % Mortality | | | | | |
|---|---|---|---|---|---|---|
| | Lygus Bug | | | Spotted Cucumber Beetle | | |
| | 3 days | 4 days | 6 days | 3 days | 4 days | 6 days |
| 2 | 100 | 100 | 100 | 60 | 100 | 100 |
| 1 | 80 | 80 | 100 | 30 | 100 | 100 |
| 0.5 | 0 | 60 | 80 | 20 | 40 | 80 |

EXAMPLE 15

Activity of Compound 7268 Against Southern Corn Rootworm

The test organism is a strain of Southern corn rootworm (*Diabrotica undecimpunctata howardi*) resistant to chlorinated hydrocarbon insecticides and test compound is Compound 7268. Duplicate samples of sand-soil mixtures are treated with appropriate volumes of test formulation to give the desired dosages. The sand-soil samples are in covered paper cups, and several hours after drenching, all cups are given a thorough shaking to provide complete and uniform mixing of the chemical throughout the soil. One day after treatment, two corn seedlings and five rootworms are placed into each cup and the lids replaced. Five days later, mortality is determined. The results are given below:

| Dosage, lb/6" A | 2.5 | 1.25 | 1 |
|---|---|---|---|
| % Mortality | 100 | 100 | 90 |

EXAMPLE 16

Systemic Activity of Compound 7268 Against Melon Aphid

The techniques used are essentially the same as for the systemic tests described above in Example 10. These test plants are cucumber seedlings; the test compound is Compound 7268; and the pest is the melon aphid (*Aphis gosyppi*).

| Dosage, lb/A | 0.5 | 0.25 | 0.125 | 0.062 |
|---|---|---|---|---|
| % Control | 100 | 100 | 100 | 100 |

EXAMPLE 17

Residual Systemic Activity of Compound 7268 Against Mexican Bean Beetle Larvae

Three furrows are opened in soil contained in 8"×10"×3" fiber pans and 12 Pinto bean seeds are evenly distributed in each furrow. The test compound is Compound 7268. Appropriate volumes of test formulation to give the desired dosages are applied over the seeds in the open furrows, and the furrows are immediately closed. At the indicated weekly intervals, one leaf is harvested from each row, placed onto water agar in a plastic Petri dish, and infested with 10 one-day-old bean beetle larvae. Mortality is determined three days later.

| Weeks After Treatment | % Mortality at Indicated Dosage, lb/A | | | |
|---|---|---|---|---|
| | 1 | 0.5 | 0.25 | Check |
| 3 | 100 | 100 | 100 | 0 |
| 7 | 100 | 100 | 100 | 10 |
| 10 | 95 | 100 | 100 | 0 |
| 11 | 95 | 70 | 95 | 0 |

EXAMPLE 18

Root-knot Nematocide Test

This test is an evaluation of the effectiveness of the compound being tested against infection by root-knot nematodes (*Meloidogyne spp.*).

Composted greenhouse soil, diluted by one-third with clean washed sand, is infested with about two grams of knotted or galled tomato roots per pot. Treatment is accomplished by applying 25 ml of the formulated compound onto the infested soil. The test formulation contains 0.056 g of Compound 7960, 1.0 ml stock emulsifier solution (0.25% Triton X-155 in acetone by volume), and 24.0 ml deionized water, giving a concentration of 2240 ppm. Lower concentrations are achieved by dilution.

After treatment with the test formulation, the soil, inoculum, and formulation are thoroughly mixed, returned to the pot, and the mixture incubated for seven days at 20° C. and constant moisture. After incubation, two seedlings of Rutgers tomato transplants and three garden nasturtium (*Nasturtium spp.*) seeds are set in each pot. Roots are removed from the soil after three weeks of growth and rated for gall (root-known nematode infection) formation. Nasturtium roots are evaluated only when necrosis of the tomato host has occurred. A rating of infection from 0 to 10 is recorded: 0=no galls or complete control, and 10=heavily galled roots comparable to controls. Each of the root systems is rated separately and the average is multiplied by 10 and subtracted from 100 to give percent nematode control. Results of the tests are shown below:

| Compound | Percent Control at Indicated Dosage, lb/A | | | | |
|---|---|---|---|---|---|
| Number | 8 | 4 | 2 | 1 | 0.5 |
| 7960 | 100 | 100 | 100 | 100 | 97 |
| 8423 | 100 | 90 | 60 | — | — |
| 8997 | 100 | 100 | 0 | — | — |
| 9026 | 90 | 70 | 60 | 30 | — |

It is to be understood that although the invention has been described with specific reference to particular embodiments thereof, it is not to be so limited, since changes and alterations therein may be made which are within the full intended scope of this invention as defined by the appended claims.

What is claimed is:

1. A composition of matter having the formula:

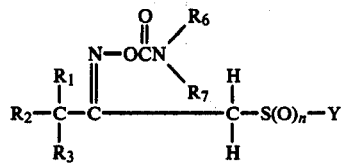

where:
R$_1$=lower alkyl or hydrogen;
R$_2$-R$_3$=lower alkyl with the proviso that R$_2$ and R$_3$ may be connected to form a cycloalkyl ring of not more than 6 carbon atoms.
R$_6$-R$_7$=hydrogen, lower alkyl or lower alkenyl;
n=0, 1 or 2; and
Y=a cyclic radical, selected from the group consisting of thiazolyl and the halogen and lower alkyl substituted thiazolyl.

2. The composition of matter according to claim 1 wherein said composition is 3,3-Dimethyl-1-[(4-tert-butylthiazol-2-yl)thio]-2-butanone O-Methylcarbamyloxime hydrobromide.

3. The composition of matter according to claim 1 wherein said composition is 3,3-Dimethyl-1-[(4,5-dihydrothiazol-2-yl)thio]-2-butanone O-Methylcarbamyloxime.

4. The composition of matter according to claim 1 wherein said composition is 3,3-Dimethyl-1-[(4-methylthiazol-2-yl)thio]-2-butanone O-Methylcarbamyloxime.

* * * * *